(12) United States Patent
Hu et al.

(10) Patent No.: US 12,123,990 B2
(45) Date of Patent: Oct. 22, 2024

(54) PARTIALLY-GATED PET IMAGING

(71) Applicant: Siemens Medical Solutions USA, Inc., Malvern, PA (US)

(72) Inventors: Jicun Hu, Knoxville, TN (US); Matthew Restivo, Knoxville, TN (US); Inki Hong, Knoxville, TN (US); Vladimir Panin, Knoxville, TN (US); Frank Kehren, Knoxville, TN (US); Michael E. Casey, Louisville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 606 days.

(21) Appl. No.: 17/303,236

(22) Filed: May 25, 2021

(65) Prior Publication Data

US 2021/0405226 A1 Dec. 30, 2021

Related U.S. Application Data

(60) Provisional application No. 62/705,457, filed on Jun. 29, 2020.

(51) Int. Cl.
*G01T 1/29* (2006.01)
*A61B 6/00* (2024.01)
*A61B 6/03* (2006.01)
*G06T 11/00* (2006.01)

(52) U.S. Cl.
CPC ............ *G01T 1/2985* (2013.01); *A61B 6/037* (2013.01); *A61B 6/5211* (2013.01); *G06T 11/005* (2013.01); *G06T 2207/10104* (2013.01)

(58) Field of Classification Search
None
See application file for complete search history.

(56) References Cited

U.S. PATENT DOCUMENTS 9,262,844 B2  2/2016 Hu
2018/0174360 A1*  6/2018 Feng .................. A61B 6/00
2019/0133542 A1*  5/2019 Li .................... A61B 6/5247

OTHER PUBLICATIONS

Martinez-Möller, Axel, et al. "Dual cardiac-respiratory gated PET: implementation and results from a feasibility study." European journal of nuclear medicine and molecular imaging 34 (2007): 1447-1454. (Year: 2007).*
Cherry, Simon R. et al., "Total-Body PET: Maximizing Sensitivity to Create New Opporunities for Clinical Research and Patient Care", Journal of Nuclear Medicine, Sep. 2017, DOI: 10.2967/jnumed.116.184028, 12 pages.

* cited by examiner

*Primary Examiner* — Vincent Rudolph
*Assistant Examiner* — Meredith Taylor

(57) ABSTRACT

Systems and methods to partially-gate PET data include acquisition of first data describing a plurality of coincidences detected during a scan of an object, each of the plurality of coincidences associated with a coincidence time and a line of response, acquisition of a motion signal associated with motion of the object during the scan, determination of lines of response which are associated with a region of the object, determination of time periods of region motion based on the motion signal, modification of the first data to remove coincidences which are associated with the determined lines of response and which are associated with a coincidence time during a time period of region motion, reconstruction of an image of the object based on the modified first data, and display of the image.

20 Claims, 6 Drawing Sheets

PARTIALLY-GATED PET IMAGING

CROSS-REFERENCE TO RELATED APPLICATIONS

This application claims the benefit of U.S. Provisional Patent Application No. 62/705,457, filed Jun. 29, 2020, the contents of which are incorporated herein for all purposes.

BACKGROUND

According to conventional positron-emission-tomography (PET) imaging, a radiopharmaceutical tracer is introduced into a patient body. Radioactive decay of the tracer generates positrons which eventually encounter electrons and are annihilated thereby. The annihilation produces two photons which travel in approximately opposite directions.

A ring of detectors surrounding a portion of the body (e.g., the torso) detects photons emitted therefrom. A coincidence is identified when two detectors disposed on opposite sides of the body detect the arrival of two photons within a particular coincidence time window. Because the two "coincident" photons travel in approximately opposite directions, the locations of the two detectors determine a Line-of-Response (LOR) along which an annihilation event may have occurred. The identified coincidences may be used to reconstruct a PET image of the portion of the body.

The portion of the body being imaged may move during imaging, for example due to cardiac and/or respiratory processes. This movement may cause a same region of the body to be located in more than one location relative to the detectors during coincidence detection. Consequently, this region may appear blurry within a PET image which is subsequently reconstructed based on the detected coincidences.

Gating may be used to address periodic motion during the acquisition of PET data. For example, according to known gating techniques, cardiac motion is monitored during coincidence detection. Periods of quiescence during the cardiac motion are identified (e.g., via an electrocardiogram signal), and a PET image is then reconstructed based only on the coincidences detected during the quiescent periods. The PET image thereby represents the imaged volume as it was positioned during the quiescent periods.

Due to the reduced number of coincidences used to reconstruct the PET image, the signal-to-noise ratio of the PET image is significantly lower than that of a non-gated PET image. However, the benefit of gating to the PET image often outweighs the drawbacks.

Long axial field of view (FOV) PET scanners allow imaging of large portions of a body using a single scanner bed position. During such imaging, some regions of a body may undergo periodic motion while others are relatively still. Performing gating as described above may therefore benefit the resulting image of the moving portions while simply reducing the signal-to-noise ratio of the other portions without any offsetting benefit.

Systems to efficiently improve PET imaging of a volume including moving and substantially-stationary portions are desired.

DETAILED DESCRIPTION

The following description is provided to enable any person in the art to make and use the described embodiments. Various modifications will remain apparent to those in the art.

Generally, some embodiments perform partial gating on acquired PET data and reconstruct a PET image based on the partially-gated data. In some embodiments, a region of a volume is identified. A PET scanner is operated to acquire PET data of the volume while motion of the region is monitored. Coincidences which are associated with the region and which occurred during a period of motion are excluded from the PET data, and a PET image is reconstructed based on the resulting PET data. LORs associated with the excluded coincidences may be scaled to account for the excluded coincidences.

Advantageously, by gating only coincidences associated with a moving region, other regions of the image can be reconstructed from a complete set of their associated coincidences. The resulting overall image will likely be visually superior to images which would have resulted from time-gating either all or none of the coincidences.

Figure 1:
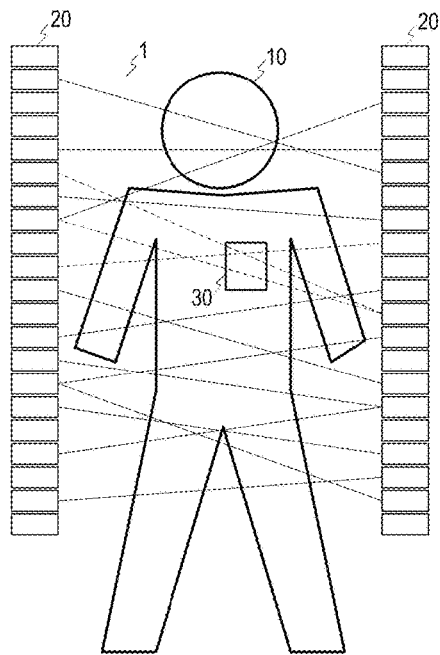
FIGS. 1 and 2 illustrate PET data acquisition according to some embodiments.
Figure 2:
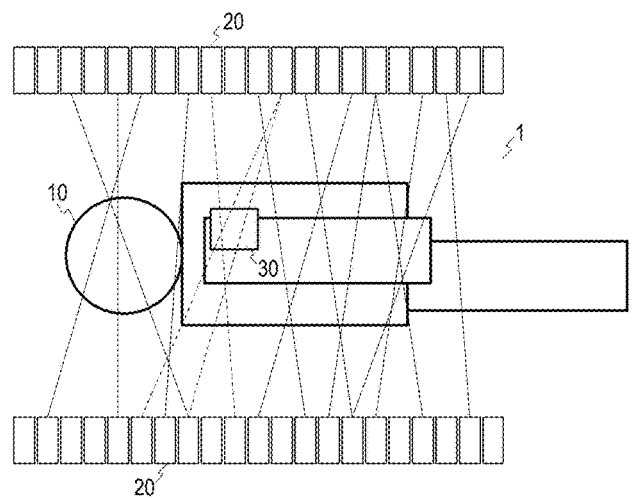

FIG. 1 and FIG. 2 illustrate detection of coincidences and corresponding LORs according to some embodiments. FIG. 1 is a top-down transaxial view of bore 1 of a PET scanner with object 10 disposed therein. Object 10 may comprise a human body, a phantom, or any other suitable object. FIG. 2 is a side transaxial view of bore 1 and object 10 of FIG. 1. The PET scanner is composed of an arbitrary number of adjacent and coaxial rings of detectors 20, and each detector 20 may comprise any number of scintillator crystals and electrical transducers.

The scintillator crystals of each detector 20 receive 511 keV photons which result from annihilation events and, in response, create photons having energies of a few electron volts. The electrical transducers convert these low-energy photons to electrical signals. According to some embodiments, the electrical transducers may comprise, for example, silicon-based photomultipliers (SiPMs), photomultiplier tubes (PMTs), or semiconductor-based detectors.

The illustrated lines connecting opposite ones of detectors 20 represent LORs associated with coincidences detected during a PET scan. A coincidence is detected when two photons arrive at two different detector crystals within a particular coincidence time window. In response, PET data is generated associating the coincidence with the two detector crystals and with an LOR connecting the two detector crystals as shown in FIGS. 1 and 2.

The LORs which pass through a given region of object 10 may be determined based on the location of the region relative to detectors 20. For instance, region 30 may represent a region in which motion is expected during PET imaging. In one example, a prior Computed Tomography (CT) scan is performed and region 30 is identified as a cardiac region based on a CT image generated from the CT scan. The location of region 30 in the CT image may then be registered to the coordinate space of the PET scanner. Since the locations of the LORs which correspond to detected coincidences are also known in the coordinate space of the PET scanner, the LORs which pass through region 30 may be determined. These LORs are represented as dashed lines in FIGS. 1 and 2.

Figure 3:
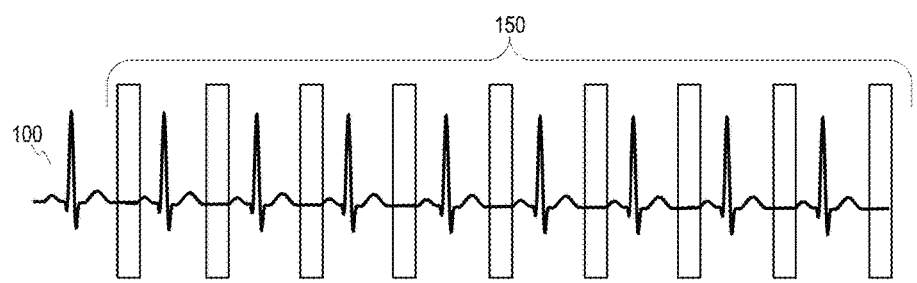
FIG. 3 illustrates gating windows with respect to a cardiac signal according to some embodiments.

According to some embodiments, and as described briefly above, the PET data acquired during the PET scan may be modified to remove coincidences which are associated with the determined LORs (i.e., the dashed lines) and which occurred while region 30 was in motion. In this regard, FIG. 3 illustrates cardiac signal 100 which was also acquired during the PET scan. Time windows 150 represent periods during which cardiac signal 100 remains relatively unchanged, and during which region 30 may be assumed to have been relatively stationary. Accordingly, the PET data acquired during the PET scan may be modified to remove coincidences which are associated with the determined LORs and which occurred outside of time windows 150.

An image is then reconstructed based on the modified PET data. Prior to reconstruction, the modified data may be normalized to account for the removed coincidences. For each LOR which passes through region 30, the remaining coincidence data (i.e., associated with coincidences which occurred within time windows 150) is scaled to account for coincidences of the LOR which were removed from the PET data (i.e., because they occurred outside of time windows 150). For example, if 30% of coincidences associated with a given LOR were removed, then the remaining coincidence data for that LOR is expanded by 30%.

Time-of-Flight (TOF) PET data associates a TOF value with each detected coincidence. The TOF value indicates a difference in the arrival time of each photon of a coincidence at its respective detector crystal. The difference may be used to estimate where the corresponding annihilation occurred along the LOR of the coincidence.

TOF PET data allows a refinement of the above process. In particular, instead of initially identifying coincidences whose LORs pass through region 30, TOF PET data allows identification of coincidences whose LORs pass through region 30 and whose estimated annihilation point falls within region 30. Coincidences are then removed from these latter coincidences based on motion-related time windows such as windows 150. Consequently, and in contrast to the non-TOF description above, coincidences associated with LORs which passed through region 30, which occurred outside time windows 150, and whose estimated annihilation point does not fall within region 30 are not removed from the PET data, thereby improving the signal-to noise-ratio of the resulting PET image.

Figure 4:
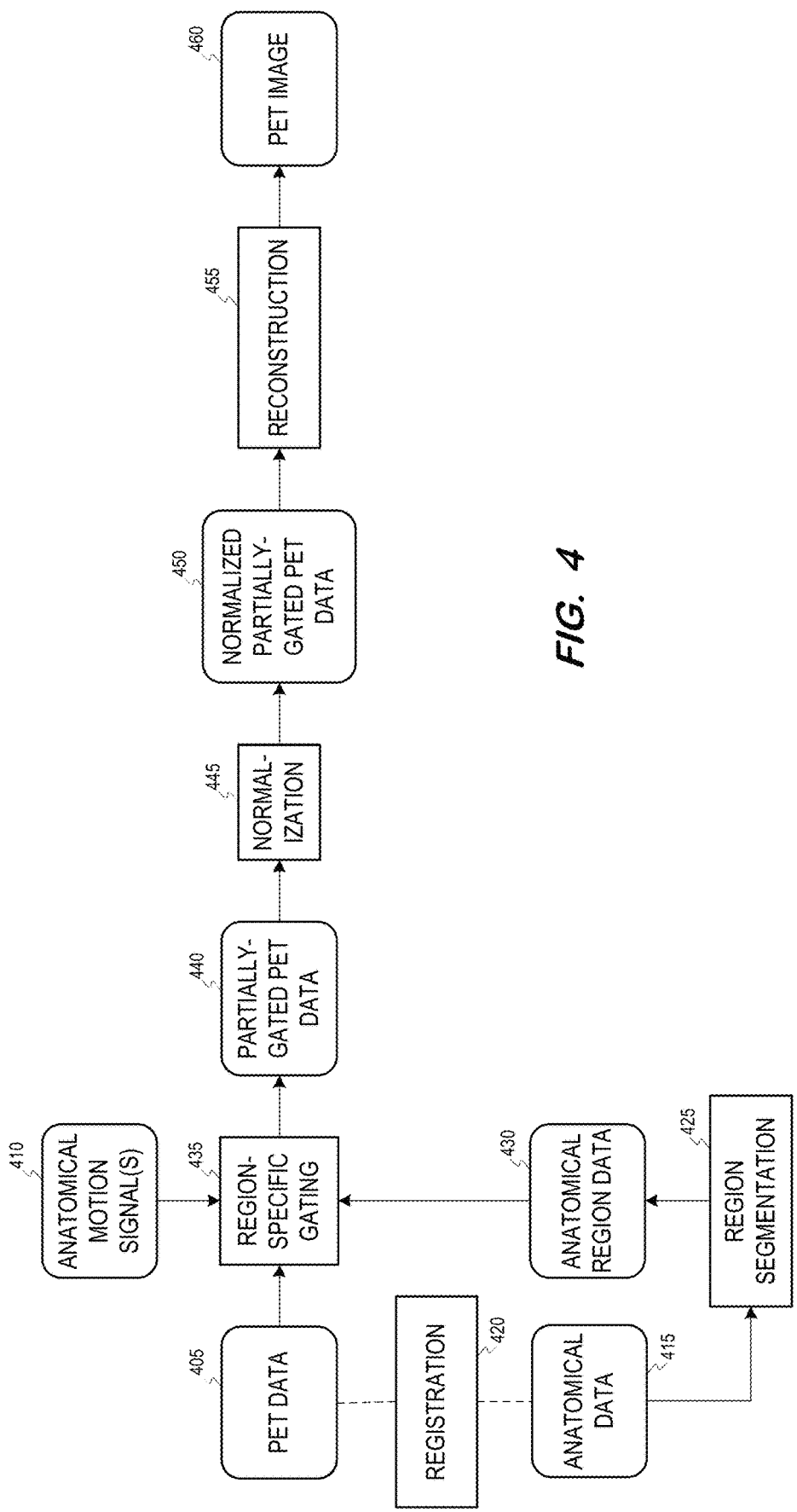
FIG. 4 is a block diagram of system for partially-gated PET imaging according to some embodiments.

FIG. 4 is a block diagram illustrating partial gating according to some embodiments. PET data 405 is acquired during a PET scan of an object as is known in the art. For example, a radionuclide tracer such as fluorodeoxyglucose (FDG) is injected into the object prior to the scan. Detectors surrounding the object detect the arrival of photons resulting from annihilations occurring within the object and coincidences are identified based on the arrivals. PET data 405 associates each identified coincidence with the two detector crystals which received the photons of the coincidence, the time of the coincidence and, in the case of TOF data, the difference in photon arrival times. PET data 405 may include additional data associated with each coincidence and with the PET scan in general.

Anatomical motion signal(s) 410 are also acquired during the PET scan. Anatomical motion signal(s) 410 may indicate motion of a region of the object over time, and may include a cardiac signal, a respiratory signal, and/or any other suitable signal. Each type of signal 410 may be acquired using any suitable means (e.g., ECG, chest belt, or calculated from PET data 405 itself) that is or becomes known.

According to some embodiments, anatomical data 415 of the object is acquired to facilitate identification and location of a region (or regions) of interest. For example, anatomical data 415 may comprise CT data acquired by a CT scan performed while the object is in position for a prior or subsequent PET scan. Registration component 420 registers anatomical data 415 and PET data 405 to a common reference frame.

Region segmentation component 425 may segment anatomical data 415 to generate anatomical region data 430. Component 425 may operate in any manner that is or becomes known. According to some embodiments, region segmentation component 425 comprises a trained machine learning model which receives data 415 and outputs anatomical region data 430. Anatomical region data 430 may indicate locations of regions in which movement is expected. In some embodiments, an operator may use anatomical region data 430 to specify regions of interest to region-specific gating component 435.

Region-specific gating component 435 gates PET data 405 based on anatomical motion signal(s) 410 and anatomical region data 430 as described herein. According to some embodiments, region-specific gating component 435 determines time windows of relatively low motion based on anatomical motion signal(s) 410. Region-specific gating component 435 also identifies coincidences of PET data 405 associated with LORs which pass through the one or more identified regions of interest (and, if PET data 405 is TOF PET data, whose estimated annihilation location lies with a region of interest). The identified coincidences which occurred outside of the determined time windows are removed from PET data 405 to generate partially-gated PET data 440.

Normalization component 445 normalizes partially-gated PET data 440 based on the removed coincidences. For each LOR associated with at least one removed coincidence, the coincidence data for that LOR within partially-gated PET data 440 is scaled to account for the removed coincidences which were associated with the LOR. Normalized partially-gated PET data 450 is then subjected to reconstruction 455 to generate PET image 460. As is known in the art, normalized partially-gated PET data 450 may be corrected for randoms and scatter prior to reconstruction 455, and reconstruction 455 may employ an attenuation map generated based on anatomical data 415.

Figure 5:
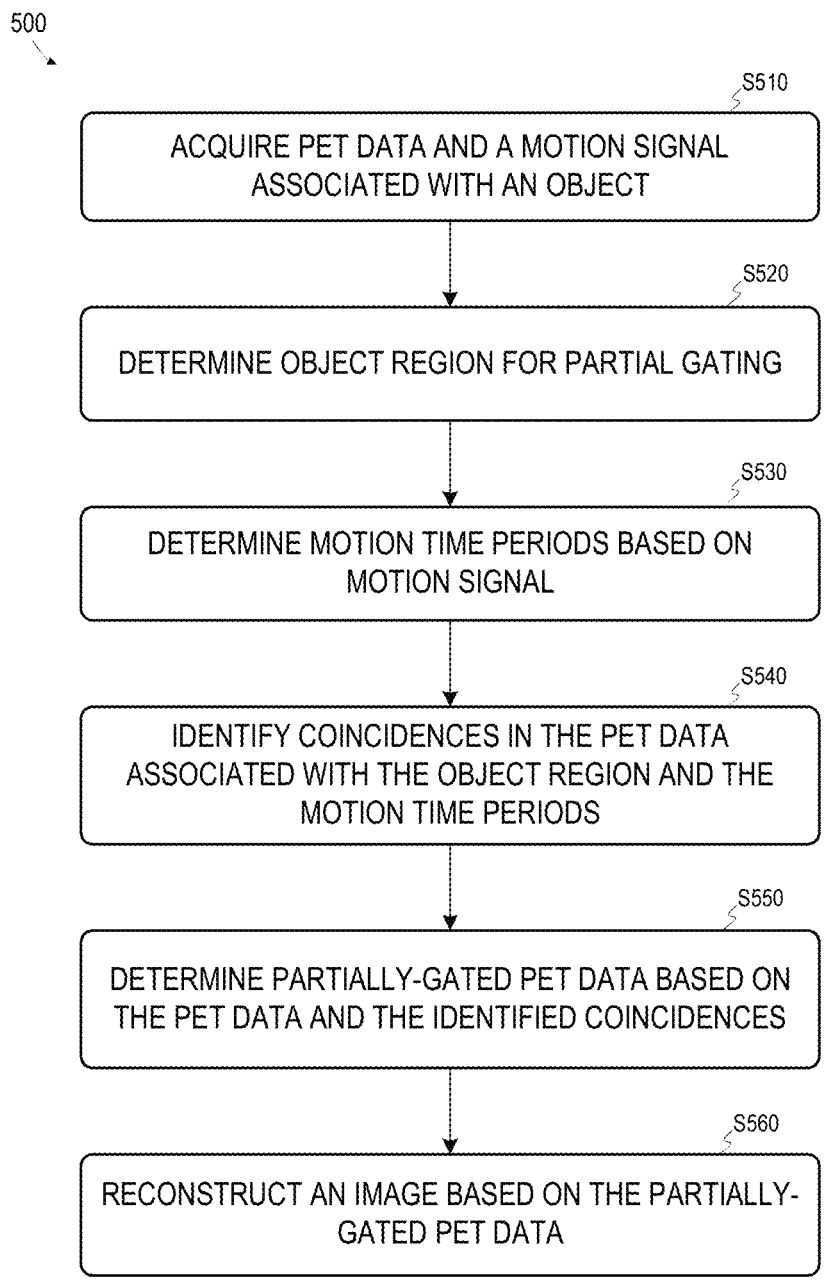
FIG. 5 comprises a flow diagram of a process to generate a partially-gated PET image according to some embodiments.

FIG. 5 comprises a flow diagram of process 500 to generate a PET image based on partially-gated PET data according to some embodiments. Process 500 and other processes described herein may be executed using any suitable combination of hardware and software. Software program code embodying these processes may be stored by any non-transitory tangible medium, including a fixed disk, a volatile or non-volatile random-access memory, a DVD, a Flash drive, and a magnetic tape, and executed by any suitable processing unit, including but not limited to one or more microprocessors, microcontrollers, processing cores, and processor threads. Embodiments are not limited to the examples described below.

PET data of an object is initially acquired at S510. As described above, a radionuclide tracer is injected into the object, photons subsequently emitted from the object are detected during a PET scan, and coincidences are identified based on the detected photons. The acquired PET data associates each identified coincidence with the two detector crystals which received the photons of the coincidence (thereby defining an LOR of the coincidence), the time of the coincidence and, in the case of TOF data, the difference in photon arrival times. According to some embodiments, the acquired PET data is in list-mode format as is known in the art.

One or more signals indicative of motion of the object during the PET scan is also acquired at S510. The one or more signals may comprise one or more of a cardiac signal, a signal produced by a respiratory monitor, a video signal depicting a region of the object and/or any other suitable signal. Each of the one or more signals may be associated with motion of one or more regions of the object over time. Two or more signals may be associated with a same region as will be described below.

A region of the object to be partially-gated is determined at S520. The determined region may comprise a region which is expected to move during the PET scan. More than one region may be determined at S520 (e.g., heart and lungs), and S520 may be performed prior to S510 in some embodiments.

According to some embodiments, CT data of the object is acquired prior to S520 and the region is determined based on the CT data. The CT data may be segmented in order to facilitate determination of an object region at S520. Segmentation may employ any known segmentation system to identify different regions (e.g., organs, structures) of the object.

Figure 6:
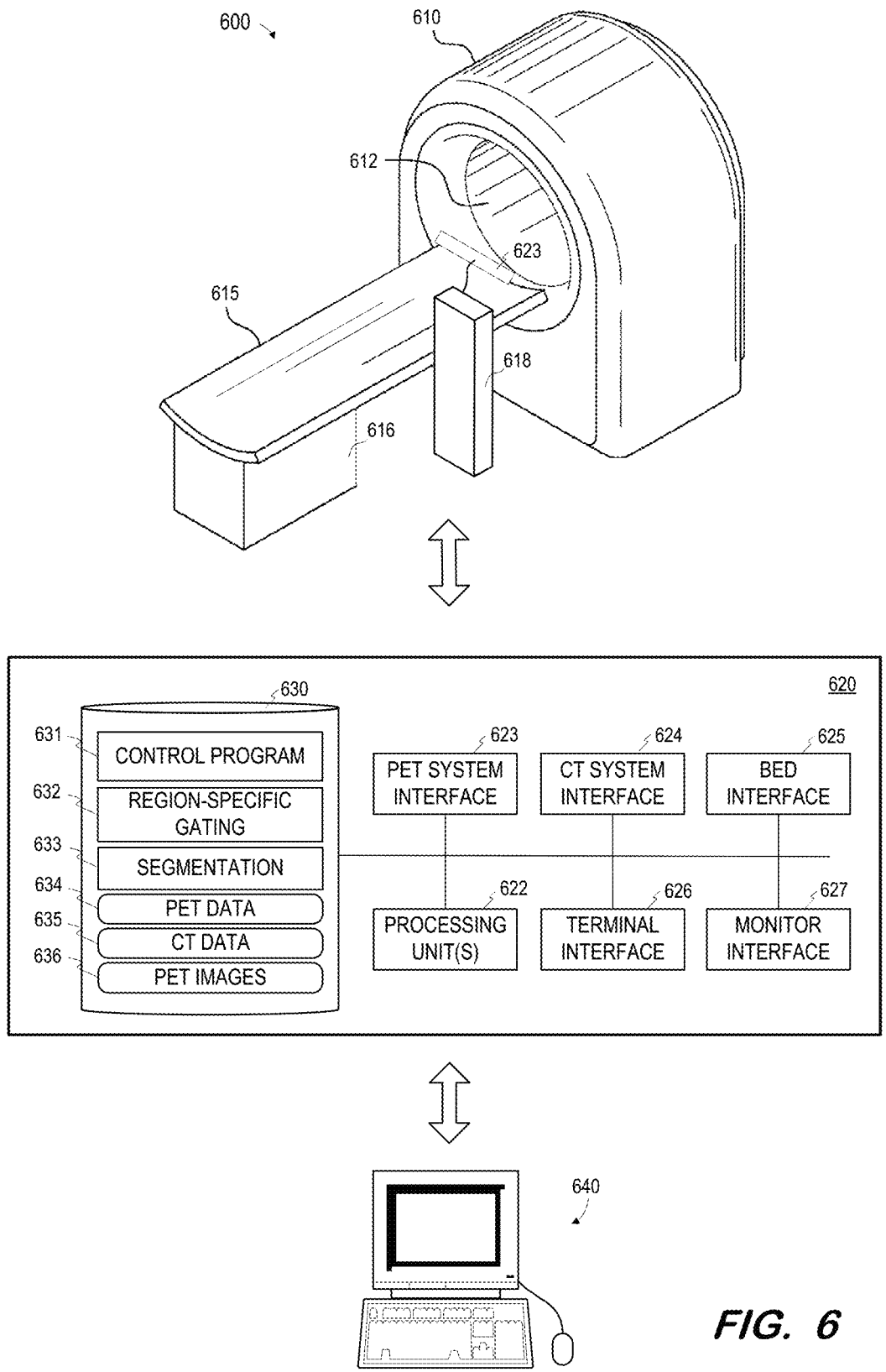
FIG. 6 is a block diagram of a PET/CT imaging system according to some embodiments.

FIG. 6 illustrates PET/CT system 600 to execute one or more of the processes described herein. Embodiments are not limited to system 600.

System 600 includes gantry 610 defining bore 612. As is known in the art, gantry 610 houses PET imaging components for acquiring PET image data and CT imaging components for acquiring CT image data. The CT imaging components may include one or more x-ray tubes and one or more corresponding x-ray detectors as is known in the art.

Anatomical motion monitor 618 may operate to generate a signal from which time periods of anatomical motion may be identified. Monitor 618 may comprise an ECG monitor, a respiratory belt, or other device. In some embodiments, monitor 618 is incorporated into gantry 610. Monitor 618 may support a wired or wireless communications link with control system 620. A hardware monitor may not be necessary if the motion signals are calculated from the list-mode PET data itself. Therefore, the motion monitor can be a computer-implemented algorithm for determining motion based on list-mode PET data.

Bed 615 and base 616 are operable to move a patient lying on bed 615 into and out of bore 612 before, during and after imaging. In some embodiments, bed 615 is configured to translate over base 616 and, in other embodiments, base 616 is movable along with or alternatively from bed 615.

Movement of a patient into and out of bore 612 may allow scanning of the patient using the CT imaging elements and the PET imaging elements of gantry 610. Accordingly, a CT scan may be conducted immediately before or after a PET scan while a patient remains in a substantially same position on bed 615. This approach facilitates registration of the CT data with the PET data.

Control system 620 may comprise any general-purpose or dedicated computing system. Accordingly, control system 620 includes one or more processing units 622 configured to execute processor-executable program code to cause system 620 to operate as described herein, and storage device 630 for storing the program code. Storage device 630 may comprise one or more fixed disks, solid-state random-access memory, and/or removable media (e.g., a thumb drive) mounted in a corresponding interface (e.g., a USB port).

Storage device 630 stores program code of control program 631. One or more processing units 622 may execute control program 631 to, in conjunction with PET system interface 623, bed interface 625, and monitor interface 627, control hardware elements to inject a radiopharmaceutical into a patient, move the patient into bore 612 past PET detectors of gantry 610, detect coincidences occurring within the patient, and acquire a motion signal. The detected coincidences may be stored in memory 630 as PET data 635.

One or more processing units 622 may also execute control program 631 to, in conjunction with CT system interface 624, cause a radiation source within gantry 610 to emit radiation toward a body within bore 612 from different projection angles, and to control a corresponding detector to acquire two-dimensional CT data 635. CT data 635 may be acquired substantially contemporaneously with the PET data as described above, and may be used for attenuation correction of contemporaneously-acquired PET data 634 as is known in the art.

Segmentation program 633 may be executed to identify regions based on CT data 635 as described above. The identified regions may be registered to a coordinate space of the PET detectors to facilitate spatial comparison of LORs within PET data 634 with locations of the identified regions.

Storage device 630 also includes region-specific gating program 632 which may be executed to partially gate PET data 634 as described in detail herein. In this regard, control program 631 may also be executed to reconstruct partially-gated PET data 634 into PET images 636 using any reconstruction algorithm that is or becomes known.

PET images 636 may be transmitted via terminal interface 626 to terminal 640 for display. Terminal 640 may comprise a display device and an input device coupled to system 620. Terminal 640 may receive user input for controlling display of the data, operation of system 600, and/or the processing described herein. In some embodiments, terminal 640 is a separate computing device such as, but not limited to, a desktop computer, a laptop computer, a tablet computer, and a smartphone.

Each component of system 600 may include other elements which are necessary for the operation thereof, as well as additional elements for providing functions other than those described herein. Each functional component described herein may be implemented in computer hardware, in program code and/or in one or more computing systems executing such program code as is known in the art. Such a computing system may include one or more processing units which execute processor-executable program code stored in a memory system.

Returning to process 500, time periods associated with motion of the object are determined based on the motion signal at S530. Since anatomical movement is not perfectly uniform or periodic, a signal analysis algorithm may be used to extract motion time periods from a motion signal at S530.

Figure 7:
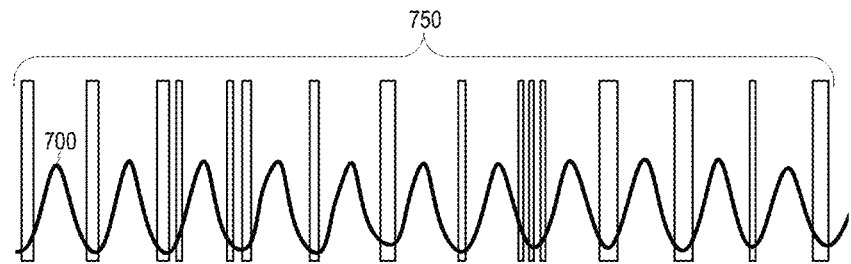
FIG. 7 illustrates gating windows with respect to a respiratory signal according to some embodiments.

For example, FIG. 7 illustrates respiration signal 700 which may be acquired at S510 during simultaneous acquisition of PET data. Time windows 750 may be identified by a signal analysis algorithm as periods during which a chest region is substantially stationary.

In a case that more than one region is determined at S520, S530 may comprise determination of region-specific motion time periods based on region-specific motion signals. In one example, first motion time periods corresponding to a heart region are determined at S530 based on an ECG signal, and second motion time periods corresponding to a lung region are also determined at S530 based on a respiratory signal.

Figure 8:
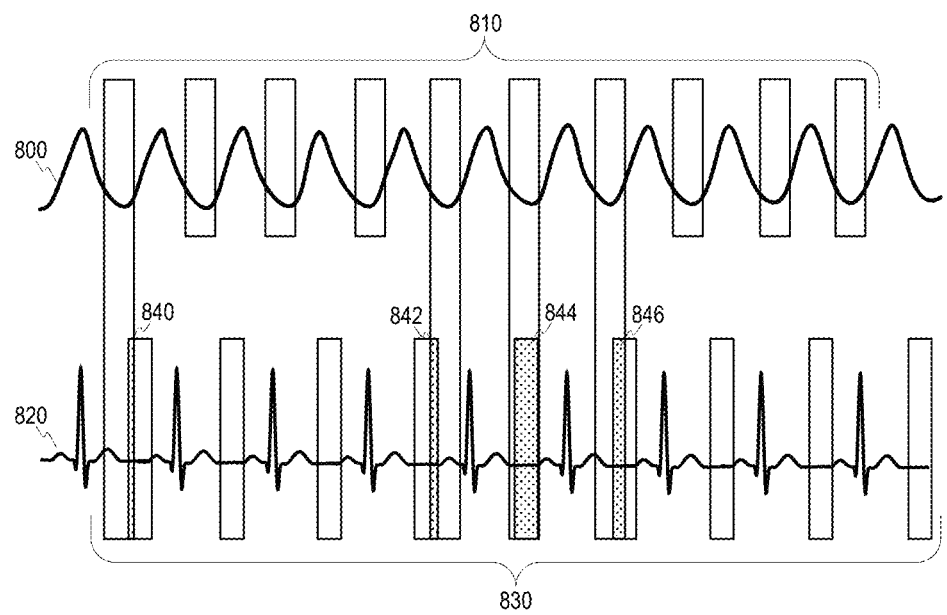
FIG. 8 illustrates gating windows with respect to a cardiac signal and a respiratory signal according to some embodiments.

Motion time periods for a single object region (e.g., chest) may be based on two or more motion signals (cardiac and respiratory). FIG. 8 illustrates respiration signal 800 and cardiac signal 820 which may be acquired at S510 during simultaneous acquisition of PET data. It may be assumed that the region of interest is the heart, and that time windows are to be determined during which both the heart and the chest are substantially stationary. Accordingly, S530 may include determination of low-motion time windows 810 of signal 800 and low-motion time windows 830 of signal 820. Time periods 840, 842, 844 and 846, which belong to both low-motion time windows 810 and low-motion time windows 830 and are depicted by shading in FIG. 8, are then determined as the low-motion time periods, with all other time periods being characterized as motion time periods.

At S540, coincidences are identified in the acquired PET data which are associated with the object region determined at S520 and the motion time periods determined at S530. As described above, such coincidences may be associated with LORs which pass through the object region (and, if the acquired PET data is TOF PET data, whose estimated annihilation location lies with the object region) and which occurred during the motion time periods determined for the object region. If a second object region is determined at S520, coincidences identified at S540 also include coincidences associated with LORs which pass through the second object region and which occurred during the motion time periods determined for the second object region. As noted above, the motion time periods determined for the second object region may differ from the motion time periods determined for the first object region.

Partially-gated PET data is determined at S550 based on the acquired PET data and the coincidences identified at S540. The partially-gated PET data may be determined at S550 by removing the identified coincidences from the acquired PET data. Removal of the coincidences may occur during list mode replay, in which the list mode data is converted into sinograms.

A sinogram is a data array which stores the coincidences detected within a single plane of detectors. A sinogram represents each LOR of each detected coincidence as an angle and a displacement from a center point lying on the scanner axis. A sinogram includes one row containing the LOR for a particular azimuthal angle φ. Each of these rows corresponds to a one-dimensional parallel projection of the tracer distribution at a different coordinate. A sinogram stores the location of the LOR of each coincidence such that all the LORs passing through a single point in the volume trace a sinusoid curve in the sinogram. A TOF sinogram includes a third dimension specifying TOF information for each coincidence.

List mode replay comprises mapping each coincidence of the list mode data to a pixel in the sinogram. The coincidences identified at S540 may be ignored during such mapping, resulting in a sinogram which includes all but the identified coincidences. In some embodiments, sinogram pixels corresponding to LORs which are associated with any of the ignored coincidences are scaled to account for the "missing" coincidences as noted above.

The partially-gated PET data (e.g., in sinogram format) is then subjected to reconstruction at S560 as is known in the art. Prior to reconstruction, the partially-gated PET data may be corrected for randoms and scatter. Reconstruction at S560 may also employ an attenuation map generated based on the above-described CT data which may have been acquired before or after S510.

Figure 10:
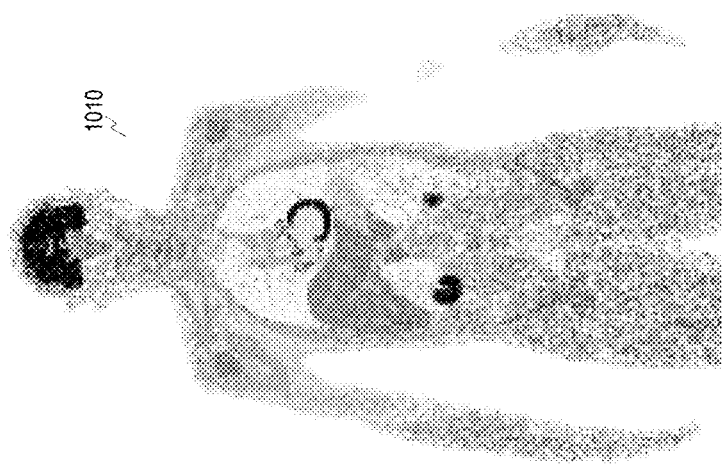
FIG. 10 is a two-dimensional PET image reconstructed based on fully-gated coincidences.
Figure 9:
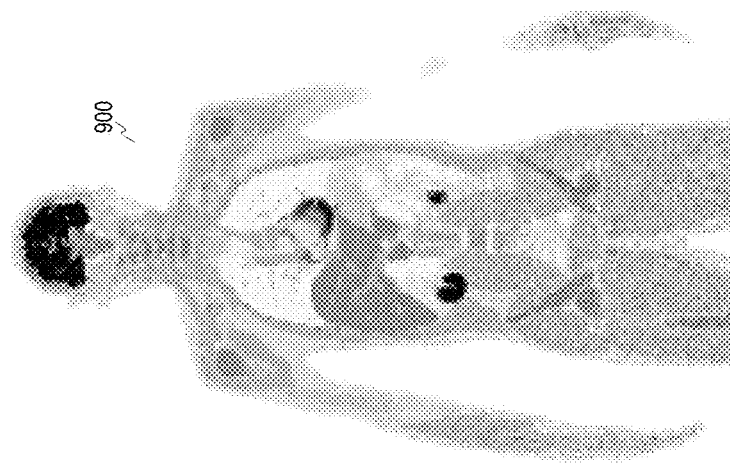
FIG. 9 is a two-dimensional PET image reconstructed based on ungated coincidences.

FIG. 9 depicts two-dimensional PET image 900 which was reconstructed based on ungated PET data. As shown, a heart region of PET image 900 exhibits artifacts due to motion of the heart during PET data acquisition. FIG. 10 depicts a two-dimensional PET image 1010 which was reconstructed based on fully-gated PET data. Specifically, PET image 1010 was reconstructed based only on coincidences which occurred during periods of low motion, without taking into account the other coincidences. The heart region is depicted more clearly in PET image 1010 than in PET image 900, but the other regions of PET image 1010 are of poorer quality than in PET image 900 due to the reduction of coincidence data for those other regions.

Figure 11:
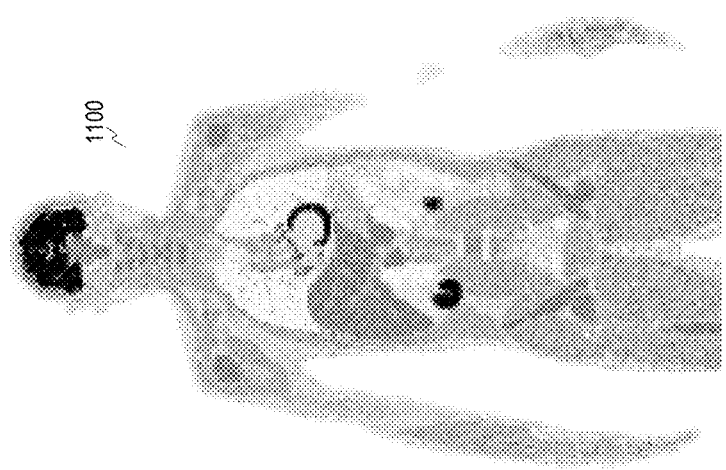
FIG. 11 is a two-dimensional PET image reconstructed based on partially-gated coincidences according to some embodiments.

FIG. 11 depicts two-dimensional PET image 1100 reconstructed based on partially-gated coincidences according to some embodiments. The heart region is depicted more clearly than in PET image 900, and the quality of the other regions of PET image 1100 is also maintained with respect to PET image 900. Accordingly, embodiments may efficiently provide improved PET images of objects which include moving regions.

Those in the art will appreciate that various adaptations and modifications of the above-described embodiments can be configured without departing from the claims. Therefore, it is to be understood that the claims may be practiced other than as specifically described herein.

What is claimed is:

1. A system comprising:
    a positron emission tomography scanner to scan an object and generate first data describing a plurality of coincidences, each of the plurality of coincidences associated with a coincidence time and a line of response;
    a motion monitor to acquire a motion signal associated with motion of the object during the scan; and
    a processing unit to:
    determine a region of the object;
    determine lines of response of the positron emission tomography scanner which pass through the region;
    determine time periods of motion of the region based on the motion signal;
    modify the first data to remove coincidences which are associated with the determined lines of response and which are associated with coincidence time during the determined time periods of motion of the region, the modified first data including coincidences which are not associated with the determined lines of response and which are associated with coincidence time during the determined time periods of motion of the region;
    reconstruct an image of the object based on the modified first data; and
    display the image.

2. The system according to claim 1, where each of the plurality of coincidences is associated with time-of-flight information, and the processing unit is to:
    determine coincidences which are associated with the determined lines of response, with time-of-flight information associated with the region, and with coincidence time occurring during the determined time periods of motion of the region, and
wherein modification of the first data comprises removal of the determined coincidences.

3. The system according to claim 1, wherein modification of the first data comprises ignoring the coincidences which are associated with the determined lines of response and which are associated with coincidence time during the determined time periods of motion of the region during list mode replay.

4. The system according to claim 1, further comprising:
a second motion monitor to acquire a second motion signal associated with second motion of the object during the scan,
wherein the time periods of motion of the region are determined based on the motion signal and the second motion signal.

5. The system according to claim 1, further comprising:
a second motion monitor to acquire a second motion signal associated with second motion of the object during the scan,
the processing unit further to:
determine a second region of the object;
determine second lines of response of the positron emission tomography scanner which pass through the second region; and
determine second time periods of second region motion based on the second motion signal,
wherein modification of the first data comprises removal of coincidences which are associated with the determined second lines of response and which are associated with coincidence time during the second determined time periods of motion of the second region.

6. The system according to claim 5, where each of the plurality of coincidences is associated with time-of-flight information, and the processing unit is to:
determine first coincidences which are associated with the determined lines of response, with time-of-flight information associated with the region, and with coincidence time occurring during the determined time periods of motion of the region; and
determine second coincidences which are associated with the second determined lines of response, with time-of-flight information associated with the second region, and with coincidence time occurring during the second determined time periods of motion of the second region, and
wherein modification of the first data comprises removal of the first and second coincidences.

7. The system according to claim 1, wherein modifying the first data comprises scaling the first data which is associated with the determined lines of response based on the removed coincidences associated with the determined lines of response.

8. A method comprising:
acquiring first data describing a plurality of coincidences detected during a scan of an object, each of the plurality of coincidences associated with a coincidence time and a line of response;
acquiring a motion signal associated with motion of the object during the scan;
determining lines of response which pass through a region of the object;
determining time periods of motion of the region based on the motion signal;
modifying the first data to remove coincidences which are associated with the determined lines of response and which are associated with coincidence time during the determined time periods of motion of the region, the modified first data including coincidences which are not associated with the determined lines of response and which are associated with coincidence time during the determined time periods of motion of the region;
reconstructing an image of the object based on the modified first data; and
displaying the image.

9. The method according to claim 8, where each of the plurality of coincidences is associated with time-of-flight information, further comprising:
determining coincidences which are associated with the determined lines of response, with time-of-flight information associated with the region, and with coincidence time occurring during the determined time periods of motion of the region, and
wherein modifying the first data comprises removal of the determined coincidences.

10. The method according to claim 9, wherein modifying the first data comprises ignoring the coincidences which are associated with the determined lines of response and which are associated with coincidence time during the determined time periods of motion of the region during list mode replay.

11. The method according to claim 8, further comprising:
acquiring a second motion signal associated with a second motion of the object during the scan,
wherein the time periods of motion of the region are determined based on the motion signal and the second motion signal.

12. The method according to claim 8, further comprising:
acquiring a second motion signal associated with a second motion of the object during the scan,
determining a second region of the object;
determining second lines of response of the positron emission tomography scanner which pass through the second region; and
determining second time periods of motion of the second region based on the second motion signal,
wherein modifying the first data comprises removal of coincidences which are associated with the determined second lines of response and which are associated with coincidence time during the determined second time periods of motion of the second region.

13. The method according to claim 12, where each of the plurality of coincidences is associated with time-of-flight information, and further comprising:
determining first coincidences which are associated with the determined lines of response, with time-of-flight information associated with the region, and with coincidence time occurring during one of the determined time periods of motion of the region; and
determining second coincidences which are associated with the second determined lines of response, with time-of-flight information associated with the second region, and with coincidence time occurring during one of the second determined time periods of motion of the second region, and
wherein modifying the first data comprises removal of the first and second coincidences.

14. The method according to claim 8, wherein modifying the first data comprises scaling the first data which is associated with the determined lines of response based on the removed coincidences associated with the determined lines of response.

15. A non-transitory computer-readable medium storing processor-executable process steps which when executed by a processing unit of a computing system, cause the computing system to:

acquire first data describing a plurality of coincidences detected during a scan of an object, each of the plurality of coincidences associated with a coincidence time and a line of response;

acquire a motion signal associated with motion of the object during the scan;

determine lines of response which are associated with a region of the object;

determine time periods of motion of the region based on the motion signal;

modify the first data to remove coincidences which are associated with the determined lines of response and which are associated with coincidence time during the determined time periods of motion of the region, the modified first data including coincidences which are not associated with the determined lines of response and which are associated with coincidence time during the determined time periods of motion of the region;

reconstruct an image of the object based on the modified first data; and display the image.

16. The medium according to claim 15, where each of the plurality of coincidences is associated with time-of-flight information, the processor-executable process steps further to cause the computing system to:

determine coincidences which are associated with the determined lines of response, with time-of-flight information associated with the region, and with coincidence time occurring during the determined time periods of motion of the region, and wherein modification of the first data comprises removal of the determined coincidences.

17. The medium according to claim 15, the processor-executable process steps further to cause the computing system to:

acquire a second motion signal associated with a second motion of the object during the scan, wherein the time periods of motion of the region are determined based on the motion signal and the second motion signal.

18. The medium according to claim 15, the processor-executable process steps further to cause the computing system to:

acquire a second motion signal associated with a second motion of the object during the scan, determine a second region of the object;

determine second lines of response of the positron emission tomography scanner which are associated with the second region; and determine second time periods of motion of the second region based on the second motion signal, wherein modification of the first data comprises removal of coincidences which are associated with the determined second lines of response and which are associated with coincidence time during the determined second time periods of motion of the second region.

19. The medium according to claim 18, where each of the plurality of coincidences is associated with time-of-flight information, the processor-executable process steps further to cause the computing system to:

determine first coincidences which are associated with the determined lines of response, with time-of-flight information associated with the region, and with coincidence time occurring during the determined time periods of motion of the region; and determine second coincidences which are associated with the second determined lines of response, with time-of-flight information associated with the second region, and with coincidence time occurring during the determined second time periods of motion of the second region, and wherein modification of the first data comprises removal of the first and second coincidences.

20. The medium according to claim 15, wherein modification of the first data comprises scaling the first data which is associated with the determined lines of response based on the removed coincidences associated with the determined lines of response.

* * * * *